US006617465B2

(12) United States Patent  
Thiele et al.

(10) Patent No.: US 6,617,465 B2
(45) Date of Patent: Sep. 9, 2003

(54) PROCESS FOR THE EPOXIDATION OF OLEFINS

(75) Inventors: George Thiele, Hanau (DE); Willi Hofen, Rodenbach (DE); Jörg Sauer, Mobile, AL (US); Thomas Haas, Frankfurt (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 10/038,776

(22) Filed: Jan. 8, 2002

(65) Prior Publication Data

US 2002/0091276 A1 Jul. 11, 2002

(30) Foreign Application Priority Data

Jan. 8, 2001 (EP) ............................................. 01100428

(51) Int. Cl.⁷ ............................................. G07D 301/12
(52) U.S. Cl. ...................................................... 549/533
(58) Field of Search .......................................... 549/533

(56) References Cited

U.S. PATENT DOCUMENTS

| 2,870,171 A | 1/1959 | Gable |
| 4,410,501 A | 10/1983 | Taramasso et al. |
| 4,833,260 A | 5/1989 | Neri et al. |
| 5,523,426 A | 6/1996 | Jubin, Jr. et al. |
| 5,591,875 A | 1/1997 | Chang et al. |
| 5,599,955 A | 2/1997 | Vora et al. |
| 5,620,935 A | 4/1997 | Thiele |
| 5,675,026 A | 10/1997 | Thiele |
| 5,760,253 A | 6/1998 | Danner et al. |
| 5,849,937 A | 12/1998 | Jubin, Jr. et al. |
| 5,849,938 A | 12/1998 | Reuter et al. |
| 5,912,367 A | 6/1999 | Chang |
| 6,042,807 A | 3/2000 | Faraj |
| 6,063,941 A | 5/2000 | Gilbeau |
| 6,372,924 B2 | 4/2002 | Thiele |

FOREIGN PATENT DOCUMENTS

| EP | 0 100 118 | 2/1984 |
| EP | 0 100 119 | 2/1984 |
| EP | 0 106 671 | 4/1984 |
| EP | 0 230 349 | 7/1987 |
| EP | 0 230 949 | 8/1987 |
| EP | 0 568 336 | 11/1993 |
| EP | 0 568 337 | 11/1993 |
| EP | 0 583 828 | 2/1994 |
| EP | 0 645 473 | 3/1995 |
| EP | 0 659 473 | 6/1995 |
| EP | 0 712 852 | 5/1996 |
| EP | 0 719 768 | 7/1996 |
| EP | 0 757 045 | 2/1997 |
| EP | 0 795 537 | 9/1997 |
| EP | 0 827 765 | 3/1998 |
| EP | 0 930 308 | 7/1999 |
| EP | 1 066 711 | 12/1999 |
| EP | 1 138 387 | 10/2001 |
| JP | 2166636 | 6/1990 |
| WO | 97/47613 | 12/1997 |
| WO | 97/47614 | 12/1997 |
| WO | 99/01445 | 1/1999 |
| WO | WO 99/07690 | 2/1999 |
| WO | WO 99/11639 | 3/1999 |
| WO | WO 00/07695 | 2/2000 |
| WO | WO 00/17178 | 3/2000 |

*Primary Examiner*—Taofiq Solola
(74) *Attorney, Agent, or Firm*—Smith, Gambrell & Russell, LLP

(57) ABSTRACT

A process for the catalytic epoxidation of olefins by means of hydrogen peroxide and a titanium zeolite catalyst, wherein the epoxidation reaction is carried out in a reaction system through which the reaction mixture flows continuously and the regeneration of deactivated catalyst is carried out by means of hydrogen peroxide in the presence of the olefin while continuing the epoxidation reaction.

24 Claims, No Drawings

PROCESS FOR THE EPOXIDATION OF OLEFINS

INTRODUCTION AND BACKGROUND

The present invention relates to a process for the epoxidation of olefins by means of hydrogen peroxide and a titanium zeolite catalyst.

Prior Art

It is known from EP-A 100 119 that propene can be reacted with hydrogen peroxide to form propene oxide when a titanium-containing zeolite is used as catalyst.

However, the catalysts have the disadvantage that they steadily lose their catalytic activity during the reaction. For the epoxidation of propene, this is described in M. G. Clerici, G. Bellussi and U. Romano, J. Catal. 129 (1991) 159–167. For this reason, methods of maintaining the catalytic activity of the catalyst by periodic regeneration of the catalyst have been developed.

WO 99/01445 relates to a process for the epoxidation of olefins by means of hydrogen peroxide in which progressive deactivation of the catalyst is countered by increasing the pressure and temperature in order to maintain a predetermined minimum conversion for as long as possible and thus to prolong the interval between two catalyst regeneration cycles. However, increasing the pressure and temperature is subject to technical limits. Thus, secondary reactions occur to an increased extent when a maximum temperature is exceeded, so that, for example, the temperature cannot be increased at will. Even when the time between two regeneration cycles can be increased, separate regeneration of the catalyst is still absolutely necessary.

It is known from Clerici et al. that the catalyst can be regenerated by calcination at 550° C. EP-A 743 094 describes a process for regeneration by calcination at a temperature of from 150 to 400° C. in the presence of molecular oxygen. Furthermore, EP-A 790 075 describes a process for regeneration in a gas stream at a temperature of from 150 to 200° C. in the absence of molecular oxygen. In all these processes, the regeneration is carried out by means of a gas phase and, owing to the high temperatures required, the catalyst generally has to be removed from the reactor used for the epoxidation, which is associated with additional costs.

It is also known from Clerici et al. that the catalyst can be regenerated by washing with a solvent at elevated temperature. However, in practice this process requires either very long times or significantly higher temperatures and can therefore not be implemented economically in industrial plants.

It is known from EP-A 757 044 that the catalyst can be regenerated by treatment with hydrogen peroxide in the absence of an olefin.

DE-A 198 05 552 teaches that this process can also be carried out with the catalyst remaining in the reactor used for the epoxidation during the regeneration. However, the process has the disadvantage that the epoxidation reaction has to be interrupted for the regeneration of the catalyst.

WO 98/18555 describes a process for regenerating a titanium zeolite catalyst which is used in the epoxidation of olefins by means of hydrogen peroxide. According to one embodiment, a solution of the oxidant which is also used for the epoxidation is employed as regeneration medium. For example, the reaction medium leaving the epoxidation reactor can, if appropriate after addition of hydrogen peroxide, be used as regeneration medium. This is largely free of unreacted olefins.

It is known from U.S. Pat. No. 5,849,937 that interruption-free operation of the epoxidation can be achieved when the reaction is carried out in a number of fixed-bed reactors connected in series and when the activity of the catalyst has dropped in one reactor, this reactor is taken out of production and replaced by a reactor containing regenerated catalyst. This procedure has the disadvantage that one more reactor and the corresponding amount of catalyst than is necessary for carrying out the epoxidation has to be kept at the ready.

All known regeneration processes have the disadvantage that the catalyst displays a step increase in activity after the regeneration and leads to increased formation of by-products formed by subsequent reactions of propylene oxide. This results in decreased yields and in problems in the operation of a continuous production plant due to the fluctuations in heat evolution and the concentrations of by-products.

It is therefore an object of the present invention to provide a process for the catalytic epoxidation of olefins by means of hydrogen peroxide and a titanium zeolite catalyst, in which process the catalytic activity of the catalyst is periodically regenerated without step changes occurring as a result of increased activity and by-product formation after the regeneration.

SUMMARY OF THE INVENTION

The above and other objects of the invention can be achieved by a process for the catalytic epoxidation of olefins by means of hydrogen peroxide and a titanium zeolite catalyst, wherein the epoxidation reaction is carried out in a reaction system through which the reaction mixture flows continuously and the regeneration of deactivated catalyst is carried out by means of hydrogen peroxide in the presence of the olefin while continuing the epoxidation reaction.

It has surprisingly been found that hydrogen peroxide is able, even in admixture with the starting olefin without interruption of the epoxidation reaction, to regenerate the deactivated catalyst. The result of the regeneration is better, the greater the concentration of the not yet reacted hydrogen peroxide in the reaction medium which comes into contact with the catalyst to be regenerated. Thus, it is particularly advantageous for the deactivated catalyst to be located close to the point at which hydrogen peroxide enters the reaction system for the regeneration.

A particularly preferred embodiment of the present invention provides a process for the catalytic epoxidation of olefins by means of hydrogen peroxide in the presence of a titanium zeolite catalyst in a reaction system through which the reaction mixture flows continuously, in which process the deactivated catalyst from the region in which the reaction product leaves the reaction system is placed near the point at which hydrogen peroxide enters, without the reaction being interrupted.

DETAILED DESCRIPTION OF THE INVENTION

The epoxidation process of the invention with regeneration of the catalyst by means of hydrogen peroxide in the presence of olefins can be carried out in various ways depending on the reaction system selected.

In one embodiment of the invention, the epoxidation reaction is carried out in a flow tube reactor in which the catalyst is fixed in the form of a fixed bed and in which a mixture of hydrogen peroxide, olefin and optionally a solvent is fed in at one end and the reaction mixture comprising the epoxide formed is taken off at the other end. The regeneration according to the invention is in this case achieved by reversal of the flow direction so that the deactivated catalyst is transposed from the end of the fixed bed to the point at which the hydrogen peroxide enters and is regenerated in this way.

In an alternative embodiment of the invention, use is made of a reaction system comprising two or more reactors connected in series in which the catalyst is in each case retained. A mixture of hydrogen peroxide, olefin and optionally a solvent is fed into the first reactor and the reaction mixture formed in this reactor is passed successively through the further reactors. If desired, further olefin can be fed in at points between the reactors. In this embodiment, regeneration according to the invention is achieved by changing the order in which the reactors are connected so that the reactor containing the deactivated catalyst becomes the first reactor in the series.

In a preferred embodiment, the reaction is carried out in two or more fixed-bed reactors connected in series and the regeneration of the catalyst is carried out by placing the last reactor in the series at the beginning of the series and operating it as the first reactor of the series. This embodiment can also be realized by configuring the series of fixed-bed reactors as a sequence of reaction zones in a common apparatus and bringing about a change in the order in which the reaction mixture flows through the zones by appropriate switching of inlets and outlets between the zones.

The regeneration of the catalyst can be carried out periodically at fixed time intervals. Alternatively, a parameter which is indicative of the activity of the catalyst can be monitored during the reaction and the regeneration of the catalyst can be initiated when the activity drops below a predetermined threshold value. The regeneration is preferably also carried out as a function of the hydrogen peroxide conversion, i.e. whenever the conversion in the overall system or in one of the reactors drops below a prescribed value. Regeneration is preferably initiated when the hydrogen peroxide conversion drops below 90%, particularly preferably 95%.

As an alternative, the catalyst activity can be monitored via the heat evolved in the exothermic epoxidation reaction. The temperature difference between a measurement point within the reactor or at the point where the reaction mixture leaves the reactor and a measurement point in the cooling medium which serves to remove the heat of reaction from the reactor can advantageously be measured. The temperature difference is approximately proportional to the amount of heat evolved. In this embodiment, the regeneration of the catalyst is preferably initiated when the temperature difference has fallen to 20%, particularly preferably 50%, of the initial temperature difference. In the present context, the initial temperature difference is the temperature difference between the two measurement points which is established after steady state operation of the continuous reaction system has been achieved after starting up the system with fresh catalyst.

The process of the present invention has various advantages compared to the prior art. In particular, the regeneration of the catalyst in the process of the invention is carried out without interrupting the reaction, so that dead times no longer occur. A process in which dead times are avoided is likewise known from U.S. Pat. No. 5,849,937, but an additional reactor together with catalyst charge is necessary in that process since a reactor is always taken out from the epoxidation process for the purposes of catalyst regeneration and the catalyst is regenerated separately. Thus, the capital costs are significantly lower compared to the teachings of U.S. Pat. No. 5,849,937.

Apart from these economic advantages, the process of the invention has the advantage that no step increase in the catalyst activity occurs, in contrast to external regeneration. The activity profile of the overall catalyst charge during continuous operation of the plant is thus significantly more uniform compared to the prior art. This leads to a constant product quality and fluctuations in the evolution of heat and the concentrations of by-products can be minimized. The process of the invention is suitable for the epoxidation of aliphatic, cycloaliphatic and aliphatic-aromatic olefinic compounds. Preference is given to using olefins having from 3 to 8 carbon atoms, particularly preferably propene and 1-butene. The olefinic compound can contain one or more functional groups, e.g. hydroxyl, halogen, alkoxy or carbalkoxy. Allyl chloride and allyl alcohol can be epoxidized readily in the process of the invention.

Catalysts suitable for the epoxidation process of the invention are crystalline, titanium-containing zeolites having the composition $(TiO_2)_x(SiO_2)_{1-x}$ where x is from 0.001 to 0.05. Preference is given to using titanium zeolites having an MFI or MEL crystal structure, known as titanium silicalite-1 and titanium silicalite-2. The titanium zeolite catalyst can be used in the form of powder or as a shaped catalyst in the form of granules, extrudates or shaped bodies. For shaping, the catalyst can contain from 1 to 99% of a binder or support material, with all binders and support materials which do not react with hydrogen peroxide or the epoxide under the reaction conditions employed for the epoxidation being suitable. Preference is given to using extrudates having a diameter of from 1 to 5 mm.

In the process of the invention, the hydrogen peroxide is used in the form of an aqueous solution having a hydrogen peroxide content of from 1 to 90% by weight, preferably from 10 to 70% by weight and particularly preferably from 30 to 50% by weight. The hydrogen peroxide can be used in the form of the commercially available, stabilized solutions. Likewise suitable are nonstabilized aqueous hydrogen peroxide solutions as are obtained in the anthraquinone process for preparing hydrogen peroxide. As an alternative, hydrogen peroxide can also be used as an organic-aqueous solution or organic solution. The hydrogen peroxide solution introduced into the epoxidation reactor is preferably a pH-controlled aqueous or aqueous-organic hydrogen peroxide solution which has been admixed with a base.

The reaction is preferably carried out in the presence of a solvent in order to increase the solubility of the olefin in the liquid phase comprising hydrogen peroxide. Suitable solvents are all solvents which are not oxidized or oxidized to only a slight extent by hydrogen peroxide under the reaction conditions selected and dissolve in water to an extent of not more than 10% by weight. Preference is given to solvents which have unlimited miscibility with water. Suitable solvents are alcohols such as methanol, ethanol or tert-butanol; glycols such as ethylene glycol, 1,2-propanediol or 1,3-propanediol; cyclic ethers such as tetrahydrofuran, dioxane or propylene oxide; glycol ethers such as ethylene glycol monomethyl ether, ethylene glycol monoethyl ether, ethylene glycol monobutyl ether or propylene glycol monomethyl ether; and ketones such as acetone or 2-butanone. Particular preference is given to adding methanol as solvent.

The process of the invention for the epoxidation of olefins is carried out at a temperature of from −10 to 100° C., preferably from 20 to 70° C. The olefin is preferably used in an excess over hydrogen peroxide to achieve a substantial hydrogen peroxide conversion. The molar ratio of olefin to hydrogen peroxide is equal to or greater than 1 and is preferably in the range from 1:1 to 10. If an organic solvent is added, the amount of solvent is preferably selected so that only a liquid phase is present in the reaction mixture. The solvent is preferably added in a weight ratio of from 1 to 20 relative to the amount of hydrogen peroxide used.

The amount of catalyst used can be varied within wide limits and is preferably chosen so that a hydrogen peroxide conversion of more than 90%, preferably more than 95%, is achieved within a period of from 1 minute to 5 hours under the reaction conditions employed.

If an olefin whose boiling point at atmospheric pressure is below the chosen reaction temperature is used, the reaction is preferably carried out under superatmospheric pressure and under an atmosphere consisting essentially of the gaseous olefin; an olefin partial pressure in the range from 0.1 to 1 MPa is suitable. The pressure is, in this case, particularly preferably in the range from 50 to 100% of the saturation vapor pressure of the olefin at the reaction temperature.

Further variations and modifications of the foregoing will be apparent to those skilled in the art and are intended to be encompassed by the claims appended hereto.

European priority application 01 100 428.0 is relied on and incorporated herein by reference.

What is claimed is:

1. A process for the catalytic epoxidation reaction of an olefin comprising reacting a reaction an olefin with hydrogen peroxide in the presence of a titanium zeolite catalyst as a reaction mixture, wherein the reacting for the epoxidation is carried out in a reaction system through which the reaction mixture flows continuously and regenerating deactivated catalyst in said reaction system by contact of deactivated catalyst with hydrogen peroxide in the presence of the olefin while continuing the epoxidation reaction to form the reaction product.

2. A process for the catalytic epoxidation reaction of an olefin comprising reacting a reaction mixture comprising an olefin and hydrogen peroxide in the presence of a titanium zeolite catalyst, wherein the reacting for the epoxidation is carried out in a reaction system through which the reaction mixture flows continuously and regenerating deactivated catalyst is carried out in said reaction system by contact of the activated catalyst with hydrogen peroxide in the presence of the olefin while continuing the epoxidation reaction to form the reaction product.

3. The process according to claim 2, wherein the deactivated catalyst is located close to a point at which hydrogen peroxide enters the reaction system.

4. The process according to claim 2, wherein the deactivated catalyst from a region in which the reaction product leaves the reaction system is placed near the point at which hydrogen peroxide enters, without the reaction being interrupted.

5. The process according to claim 3, wherein the deactivated catalyst from a region in which the reaction product leaves the reaction system is placed near the point at which hydrogen peroxide enters, without the reaction being interrupted.

6. The process according to claim 2, wherein the epoxidation reaction is carried out in a flow tube reactor in which the catalyst is fixed in the form of a fixed bed and in which a mixture of hydrogen peroxide, olefin and optionally a solvent is fed in at one end and the reaction mixture comprising the epoxide formed is taken off at the other end and the regenerating is achieved by reversal of flow direction of the reaction mixture so that the deactivated catalyst is transposed from an end of the fixed bed to the point at which the hydrogen peroxide enters the reaction system.

7. The process according to claim 3, wherein the epoxidation reaction is carried out in a flow tube reactor in which the catalyst is fixed in the form of a fixed bed and in which a mixture of hydrogen peroxide, olefin and optionally a solvent is fed in at one end and the reaction mixture comprising the epoxide formed is taken off at the other end and the regenerating is achieved by reversal of flow direction of the reaction mixture so that the deactivated catalyst is transposed from an end of the fixed bed to the point at which the hydrogen peroxide enters the reaction system.

8. The process according to claim 4, wherein the epoxidation reaction is carried out in a flow tube reactor in which the catalyst is fixed in the form of a fixed bed and in which a mixture of hydrogen peroxide, olefin and optionally a solvent is fed in at one end and the reaction mixture comprising the epoxide formed is taken off at the other end and the regenerating is achieved by reversal of flow direction of the reaction mixture so that the deactivated catalyst is transposed from an end of the fixed bed to the point at which the hydrogen peroxide enters the reaction system.

9. The process according to claim 2, wherein the reaction system comprises two or more reactors connected in series in which the catalyst is in each case retained, where a mixture of hydrogen peroxide, olefin and optionally a solvent is fed into a first reactor and the reaction mixture formed in this reaction is passed successively through further reactors and regenerating is achieved by changing the order in which the reactors are connected so that the reactor containing the deactivated catalyst becomes the first reactor in a series.

10. The process according to claim 3, wherein the reaction system comprises two or more reactors connected in series in which the catalyst is in each case retained, where a mixture of hydrogen peroxide, olefin and optionally a solvent is fed into a first reactor and the reaction mixture formed in this reaction is passed successively through further reactors and regenerating is achieved by changing the order in which the reactors are connected so that the reactor containing the deactivated catalyst becomes the first reactor in a series.

11. The process according to claim 4, wherein the reaction system comprises two or more reactors connected in series in which the catalyst is in each case retained, where a mixture of hydrogen peroxide, olefin and optionally a solvent is fed into a first reactor and the reaction mixture formed in this reaction is passed successively through further reactors and regenerating is achieved by changing the order in which the reactors are connected so that the reactor containing the deactivated catalyst becomes the first reactor in a series.

12. The process according to claim 2, wherein the reaction is carried out in two or more fixed-bed reactors connected in series into which a mixture of hydrogen peroxide, olefin and optionally a solvent is fed at one end and the reaction mixture comprising the epoxide formed is taken off at the other end and regenerating of the deactivated catalyst is achieved by placing the last reactor in the series at the beginning of the series and operating it as first reactor of the series.

13. The process according to claim 3, wherein the reaction is carried out in two or more fixed-bed reactors connected in series into which a mixture of hydrogen peroxide, olefin and optionally a solvent is fed at one end and the reaction mixture comprising the epoxide formed is taken off at the other end and regenerating of the deactivated catalyst is achieved by placing the last reactor in the series at the beginning of the series and operating it as first reactor of the series.

14. The process according to claim 4, wherein the reaction is carried out in two or more fixed-bed reactors connected in series into which a mixture of hydrogen peroxide, olefin and optionally a solvent is fed at one end and the reaction mixture comprising the epoxide formed is taken off at the other end and regenerating of the deactivated catalyst is achieved by placing the last reactor in the series at the beginning of the series and operating it as first reactor of the series.

15. The process according to claim 2, further comprising locating the catalyst in a sequence of reaction zones connected in series in a common apparatus, feeding a mixture of hydrogen peroxide, olefin and optionally a solvent at one end of a reaction zone and the reaction mixture comprising the epoxide formed is taken off at the other end of said reaction zone, changing the order in which the reaction mixture flows through the zones by appropriate switching off inlets and outlets between the zones so that the reaction mixture flows through the zone containing the deactivated catalyst as a first reaction zone.

16. The process according to claim 3, further comprising locating the catalyst in a sequence of reaction zones connected in series in a common apparatus, feeding a mixture of hydrogen peroxide, olefin and optionally a solvent at one end of a reaction zone and the reaction mixture comprising the epoxide formed is taken off at the other end of said reaction zone, changing the order in which the reaction mixture flows through the zones by appropriate switching off inlets and outlets between the zones so that the reaction mixture flows through the zone containing the deactivated catalyst as a first reaction zone.

17. The process according to claim 4, further comprising locating the catalyst in a sequence of reaction zones connected in series in a common apparatus, feeding a mixture of hydrogen peroxide, olefin and optionally a solvent at one end of a reaction zone and the reaction mixture comprising the epoxide formed is taken off at the other end of said reaction zone, changing the order in which the reaction mixture flows through the zones by appropriate switching off inlets and outlets between the zones so that the reaction mixture flows through the zone containing the deactivated catalyst as a first reaction zone.

18. The process according to claim 9, wherein further olefin is fed in at points between the reactors.

19. The process according to claim 12, wherein further olefin is fed in at points between the reactors.

20. The process according to claim 15, wherein further olefin is fed in at points between the reaction zones.

21. The process according to claim 2, wherein the regenerating of the catalyst is carried out periodically at fixed time intervals.

22. The process according to claim 2, wherein a parameter which is indicative of the activity of the catalyst is monitored during the reaction and the regeneration of the catalyst is initiated when the activity drops below a predetermined threshold value.

23. The process according to claim 22, wherein the parameter is selected from among hydrogen peroxide conversion and evolution of heat.

24. The process according to claim 2, further comprising carrying out the process without taking a reactor out of production and without replacing catalyst.

* * * * *

UNITED STATES PATENT AND TRADEMARK OFFICE
CERTIFICATE OF CORRECTION

PATENT NO.     : 6,617,465 B2
DATED          : September 9, 2003
INVENTOR(S)    : Thiele, Georg et al.

It is certified that error appears in the above-identified patent and that said Letters Patent is hereby corrected as shown below:

<u>Title page,</u>
Item [75], Inventors, should read as follows:
-- Inventors:   Georg Thiele, Hanau (DE); Willi Hofen, Rodenbach (DE); Jörg Sauer, Mobile, AL (US); Thomas Haas, Frankfurt (DE) --

<u>Column 5,</u>
Line 30, delete "a reaction".

Signed and Sealed this

Sixth Day of April, 2004

JON W. DUDAS
*Acting Director of the United States Patent and Trademark Office*